United States Patent [19]

Kluge et al.

[11] 4,232,038

[45] Nov. 4, 1980

[54] 5-ALKYLSULFINYLBENZOYL- AND 5-ALKYLSULFONYLBENZOYL-1,2-DIHYDRO-3H-PYRROLO[1,2-A]PYRROLE-1-CARBOXYLIC ACIDS

[75] Inventors: Arthur F. Kluge, Los Altos; Joseph M. Muchowski, Sunnyvale, both of Calif.

[73] Assignee: Syntex (U.S.A.) Inc., Palo Alto, Calif.

[21] Appl. No.: 71,443

[22] Filed: Aug. 31, 1979

[51] Int. Cl.$^2$ .................. C07D 487/04; A61K 31/40
[52] U.S. Cl. .............. 424/274; 260/326.25; 260/326.46; 260/326.5 S; 260/326.5 SF; 260/376.62
[58] Field of Search ............ 260/326.25, 326.31; 424/274

[56] References Cited

U.S. PATENT DOCUMENTS

| 4,087,539 | 5/1978 | Muchowski et al. | 260/326.25 |
| 4,089,969 | 5/1978 | Muchowski et al. | 260/326.25 |
| 4,097,579 | 6/1978 | Muchowski et al. | 260/326.25 |
| 4,140,698 | 2/1979 | Van Horn et al. | 260/326.25 |

OTHER PUBLICATIONS

Kochetkov et al.; Chem. Abs. vol. 55:1574g (1961).
Brandange et al.; Chem. Abs. vol. 76:25024t (1972).
Carelli et al.; Chem. Abs. vol. 59:7463g (1963).

Primary Examiner—Mary C. Lee
Attorney, Agent, or Firm—Tom M. Moran; Alan M. Krubiner

[57] ABSTRACT

Novel 5-alkylsulfinylbenzoyl- and 5-alkylsulfonylbenzoyl,2-dihydro-3H-pyrrolo[1,2-a]pyrrole-1-carboxylic acid compounds represented by the formula

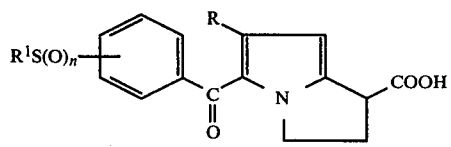

and the pharmaceutically acceptable, non-toxic esters and salts thereof, wherein n is 1 or 2, R is hydrogen or a lower alkyl group containing from 1-4 carbon atoms and $R^1$ is a lower alkyl group having from 1-4 carbon atoms at the ortho, meta or para postions of the benzoyl group and process for the production of such compounds. These compounds are useful as anti-inflammatory, analgesic and antipyretic agents and as smooth muscle relaxants.

19 Claims, No Drawings

5-ALKYLSULFINYLBENZOYL- AND 5-ALKYLSULFONYLBENZOYL-1,2-DIHYDRO-3H-PYRROLO[1,2-A]PYRROLE-1-CARBOXYLIC ACIDS

BACKGROUND OF THE INVENTION

1. Field

The present invention relates to certain novel 5-alkylsulfinyl- and 5-alkylsulfonylbenzoyl-1,2-dihydro-3H-pyrrolo[1,2-a]pyrrole-1-carboxylic acid compounds, pharmaceutical compositions containing same, a process for making the compounds and the use of the compounds to treat inflammation, and pyrexia and pain in mammals. The compounds are also smooth muscle relaxants.

2. Prior Art

Compounds of the formula

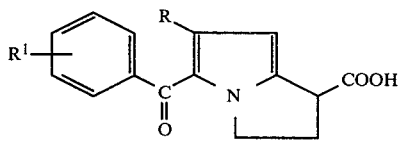

wherein R is hydrogen or lower alkyl of 1–4 carbons and $R^1$ is lower alkyl of 1–4 carbons, alkoxy of 1–4 carbons, chloro, fluoro or bromo are set forth in U.S. Pat. No. 4,089,969 as having analgetic, anti-inflammatory and antipyretic activity.

The compounds of this invention are patentably distinct from those of the '969 patent.

SUMMARY AND DISCUSSION

This invention relates to novel 5-alkylsulfinylbenzoyl- and 5-alkylsulfonylbenzoyl-1,2-dihydro-3H-pyrrolo[1,2-a]pyrrole-1-carboxylic acids represented by the formula

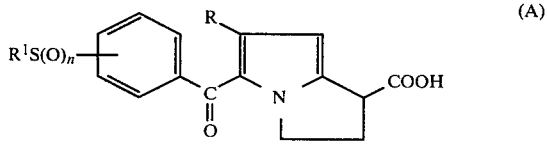

and the individual (l)-acid isomers and the (d)-acid isomers thereof and the pharmaceutically acceptable, non-toxic esters and salts thereof, wherein n is 1 or 2, R represents hydrogen or a lower alkyl group having from 1–4 carbon atoms and $R^1$ represents a lower alkyl group having from 1 to 4 carbon atoms, the $R^1S(O)_n$ group being at the ortho, meta or para positions of the benzoyl group.

The compounds of the present invention as described above and more fully below, and derivatives thereof, exhibit anti-inflammatory, analgesic and anti-pyretic activities and thus are useful in the treatment of inflammation, pain and/or pyrexia in mammals, as described hereinafter in detail. They are also smooth muscle relaxants.

The compounds of the invention are prepared by hydrolyzing an ester or by converting a 1-nitrile to the acid by treatment with an acid or base. A more complete discussion is set forth hereafter.

The term "pharmaceutically acceptable, non-toxic esters and salts" as used herein refers to "alkyl esters" derived from hydrocarbons of branched or straight chain having from 1 to 12 carbon atoms and salts derived from pharmaceutically acceptable non-toxic inorganic and organic bases, respectively.

Typical alkyl ester groups are, for example, methyl, ethyl, propyl, isopropyl, butyl, t-butyl, isoamyl, pentyl, isopentyl, hexyl, octyl, nonyl, isodecyl, 6-methyldecyl and dodecyl esters.

Salts derived from inorganic bases include sodium potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminioethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purine, piperazine, piperidine, N-ethylpiperidine, polyamine resins and the like. Particularly preferred organic non-toxic bases are isopropylamine, diethylamine, ethanolamine, piperidine, tromethamine, dicyclohexylamine, choline and caffeine.

The novel compounds of Formulas (A) and (XI) depicted below exist as pairs of optical isomers (or enantiomorphs), i.e., a (dl) mixture. However, each optical isomer as well as the (dl) mixtures thereof are included within the present invention.

A preferred sub-grouping is that of the compounds of Formula (A) and the esters and pharmaceutically acceptable salts thereof wherein R is hydrogen and, preferably, $R^1$ is methyl.

Another subgrouping, is the compounds of Formula (A) and the esters and pharmaceutically acceptable salt thereof wherein the $R^1S(O)_n$ is at the para-position and, preferably, $R^1$ is methyl.

The most preferred compounds are those of Formula (A) wherein R is hydrogen, $R^1$ is methyl, n is 1 or 2 and the $R^1S(O)_n$ is at the para position.

PROCESS

The novel compounds of the present invention can be prepared by a process illustrated by the following reaction sequence:

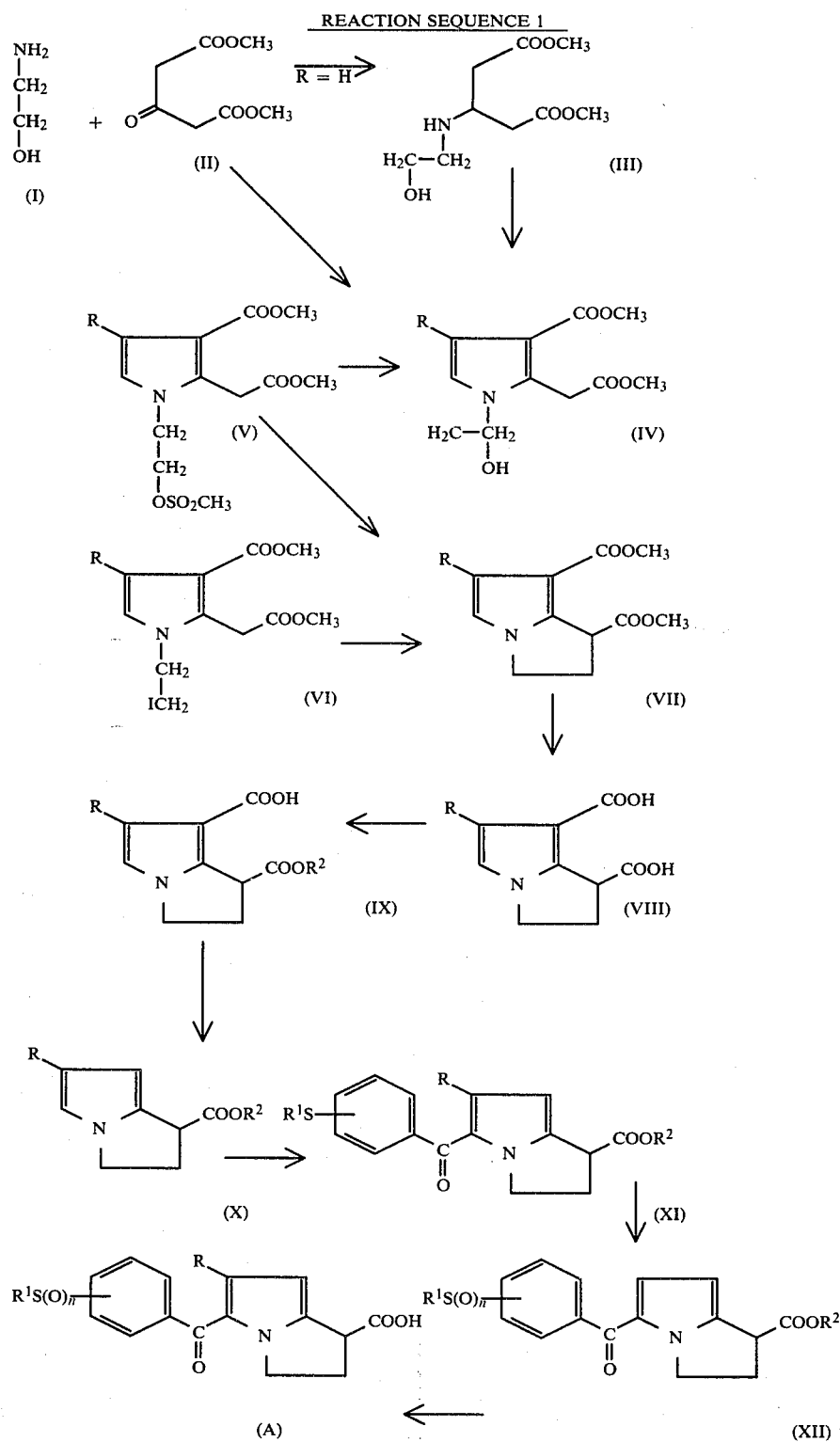

wherein R and R[1] have the above-indicated meaning and R[2] is a lower alkyl group of 1–4 carbon atoms, e.g., methyl, ethyl, isopropyl and n-butyl.

In practicing the process outlined above, for the preparation of the compound of Formula (IV) wherein R is hydrogen, equimolecular amounts of ethanolamine (I) and dimethyl 1,3-acetonedicarboxylate (II) are reacted at a temperature of from about 0° to about room temperature, to readily form a solution of the vinylamine of Formula (III), which is then treated, preferably in situ, in suitable inert organic solvent, under anhydrous conditions, with 2-bromoacetaldehyde or 2-chloroacetaldehyde, at from about 40° to about 100° C. for a period of time from about 30 minutes to about 16 hours. Suitable solvents for this reaction are the aprotic solvents such as acetonitrile, tetrahydrofuran, dimethoxyethane, chloroform, dichloromethane and the like. In the preferred embodiments, the reaction is conducted in acetonitrile solution, at reflux temperature for about 1 hour. The 2-bromo-(chloro)-acetaldehyde reagents are known compounds, or can be obtained by pyrolysis of the corresponding diethyl acetals in the presence of oxalic acid dihydrate.

To prepare the compounds of Formula (IV) wherein R is a lower alkyl group, preferably straght chain, having 1–4 carbon atoms, an aqueous mixture of ethanolamine (I) and dimethyl 1,3-acetonedicarboxylate (II) is treated with a compound of the formula

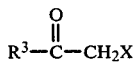

wherein X is bromo or chloro and $R^3$ is lower alkyl group, preferably straight chain, of from 1–4 carbon atoms, and most preferably 1-bromoacetone, 1-bromo-2-butanone, 1-bromo-2-pentanone, and 1-bromo-2-hexanone, at from about −10° to about 100° C. for a period of time from about 30 minutes to about 16 hours. In the preferred embodiment the reaction is conducted at a temperature of from about −10° C. to about room temperature for from about 1 hour to about 6 hours. The

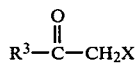

reagents are known compounds.

Esterification of compound (IV) with methanesulfonyl chloride in the presence of a tertiary amine, i.e., triethylamine, pyridine and the like, optionally in the presence of a cosolvent such as dichloromethane, at a temperature of from about −10° C. to about room temperature, for about 10 minutes to about 2 hours produces the corresponding mesylate of Formula (V), which is converted into the corresponding N-(2-iodoethyl)-pyrrole of Formula (VI) by reaction with sodium iodide in acetonitrile solution, at reflux temperature for from about 1 to about 10 hours.

Upon reaction of the iodoethyl compounds of Formula (VI) with sodium hydride in a suitable inert organic solvent such as dimethylformamide there are obtained dimethyl-1,2-dihydro-3H-pyrrolo[1,2-a]pyrrole-1,7-dicarboxylate and the 6-alkyl substituted derivatives thereof (VII). This cyclization is conducted under an inert atmosphere, i.e., under argon or nitrogen atmosphere, at temperatures of the order of from about 15° to about 40° C., for a period of time of from about 15 minutes to about 4 hours. Best results are obtained conducting the reaction at room temperature, for about 20 minutes when R is hydrogen.

Alternatively, the compounds of Formula (VII) can be prepared by direct cyclization of the mesylate (V), with sodium hydride in dimethylformamide solution, at from about −10° C. to about room temperature, for from about 20 minutes to about 2 hours.

Basic hydrolysis of a compound of Formula (VII) with an alkali metal hydroxide or alkali metal carbonate, e.g., sodium hydroxide, potassium hydroxide, sodium carbonate, potassium carbonate and the like in an aqueous lower aliphatic alcohol, e.g., methanol or ethanol, at a temperature of between room temperature and reflux, for from about 4 to about 24 hours, affords the corresponding free diacid of Formula (VIII), i.e., 1,2-dihydro-3H-pyrrolo[1,2-a]pyrrole-1,7-dicarboxylic acid and the 6-alkyl derivatives thereof. The hydrolysis is preferably carried out using aqueous methanolic potassium hydroxide, at reflux temperature for about 10 hours.

The carboxylic acid group at the C-1 position in compound (VIII) is then selectively esterified by treatment with a lower aliphatic alcohol, e.g., methanol, ethanol, isopropanol, n-butanol and the like in the presence of hydrogen chloride, to produce the corresponding alkyl 1,2-dihydro-3H-pyrrolo[1,2-a]pyrrole-1-carboxylate-7-carboxylic acid of Formula (IX). The reaction is conducted at a temperature of from about 0° to about 50° C., for about 1 to about 4 hours.

Decarboxylation of the monoesterified compounds (IX) to the corresponding compounds of Formula (X), the key intermediates in the process for obtaining the compounds of the present invention, is achieved by heating (IX) at an elevated temperature, of the order of from about 230° to about 280° C., for a period of time sufficient to complete the reaction, The course of the reaction can be followed by the rate of carbon dioxide evolution and t.l.c. analysis, decarboxylation being generally completed within from about 45 to about 90 minutes. The reaction product, namely, alkyl 1,2-dihydro-3H-pyrrolo[1,2-a]pyrrole-1-carboxylate and the 6-alkyl derivatives thereof (X) can be purified by chromatographic techniques. Alternatively, and particularly for the decarboxylation of small batches of compound (IX), the reaction product (X) can be distilled directly from the reaction vessel.

Condensation of a compound (X) with either an acid chloride of the formula

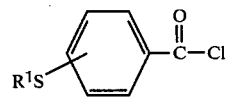

or a reagent prepared from an amide of the formula

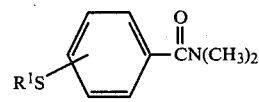

and phosphorus oxychloride wherein $R^1$ has the above-indicated meaning, affords the corresponding alkyl 5-benzoyl-1,2-dihydro-3H-pyrrolo[1,2-a]pyrrole-1-carboxylate (XI). This is done by following process conditions set forth in U.S. Pat. No. 4,089,969 and conditions set forth in Examples hereafter.

In the preferred embodiment of this process, this condensation is carried out by adding a solution of compound (X) in a sutiable solvent to a previously refluxed mixture of 1.1 to 5 molar equivalents of both the desired amide and phosphorus oxychloride in the same solvent, refluxing the reaction mixture thus obtained for from about 6 to about 72 hours under an argon atmosphere and thereafter adding thereto from about 3 to about 10 molar equivalents of sodium acetate, followed by an additional reflux period for from about 4 to about 6 hours.

Adequate solvents for this reaction are the halogenated hydrocarbons such as dichloromethane, 1,2- dichloroethane, chloroform, carbon tetrachloride and the like, dimethoxyethane and tetrahydrofuran. The preferred solvent is 1,2-dichloroethane.

Representative of the N,N-dimethyl benzamides which can be used are:
N,N-dimethyl-p-methylthiobenzamide;
N,N-dimethyl-o-methylthiobenzamide;
N,N-dimethyl-m-methylthiobenzamide;
N,N-dimethyl-o-ethylthiobenzamide;
N,N-dimethyl-m-ethylthiobenzamide;
N,N-dimethyl-p-ethylthiobenzamide;
N,N-dimethyl-p-propylthiobenzamide;
N,N-dimethyl-o-isopropylthiobenzamide;
N,N-dimethyl-m-isopropylthiobenzamide;
N,N-dimethyl-p-butylthiobenzamide;
N,N-dimethyl-o-isobutylthiobenzamide;
N,N-dimethyl-m-isobutylthiobenzamide;
N,N-dimethyl-p-isobutylthiobenzamide;
N,N-dimethyl-m-(t-butylthio)benzamide; and
N,N-dimethyl-p-(t-butylthio)benzamide.

These amides are known, commercially available compounds or can be prepared in a conventional manner from the corresponding acids i.e., by conversion into the following acid chlorides followed by treatment with dimethylamine:
p-methylthiobenzoyl chloride;
o-methylthiobenzoyl chloride;
m-methylthiobenzoyl chloride;
o-ethylthiobenzoyl chloride;
m-ethylthiobenzoyl chloride;
p-ethylthiobenzoyl chloride;
p-propylthiobenzoyl chloride;
o-isopropylthiobenzoyl chloride;
m-isopropylthiobenzoyl chloride;
p-butylthiobenzoyl chloride;
o-isobutylthiobenzoyl chloride;
m-isobutylthiobenzoyl chloride;
m-isobutylthiobenzoyl chloride;
m-(t-butylthio)benzoyl chloride; and
p-(t-butylthio)benzoyl chloride.

The compounds of Formula (XI) are readily converted to the compounds of Formula (XII) by oxidation of the alkylthio group to the alkyl sulfinyl or alkylsulfonyl group. This is readily accomplished by reacting the compounds of Formula (XI) with a suitable oxidizing agent such as m-chloroperbenzoic acid, peracetic acid, perphthalic acid, trifluoroperacetic acid, and hydrogen peroxide in acetic acid, at low temperatures such as about $-10°$ C. to about $10°$ C., preferably about $0°-5°$ C. Of these m-chloroperbenzoic acid is preferred. The degree of oxidation is controlled by adjusting the mole ratio of the oxidizing agent to the alkylthio compound of Formula (XI). If a compound of Formula (XII) wherein n is 1 is desired, an approximately equimolar amount of the oxidizing agent is used, i.e., a mole ratio of about 1.0 to 1.1. If, on the other hand, the compounds of Formula (XII) wherein n is 2 are desired, the mole ratio of the oxidizing agent to the compound of Formula (XI) is about 2.0 to 2.2. In either case, the reaction is preferably carried out in an inert organic solvent such as a halogenated aliphatic hydrocabon or an inert aliphatic or aromatic hydrocarbon. Chloroform has been found to be particularly useful. Generally, a solution of the oxidizing agent will be added to a solution of the alkylthio compound over a short (10–20 minutes) period of time while the reactants are agitated. The reaction is complete in less than about two hours at $0°$ C.

Upon alkaline hydrolysis of the alkyl ester group in a compound of Formula (XI) there is obtained the corresponding free acid of Formula (A). This hydrolysis is effected in a conventional manner, with an alkali metal hydroxide or alkali metal carbonate, e.g., sodium hydroxide, potassium hydroxide, sodium carbonate, potassium carbonate and the like, in an aqueous lower aliphatic alcohol, e.g., methanol, ethanol and the like, at a temperature of from about room temperature to reflux, for from about 15 minutes to about 2 hours, under an inert atmosphere. In the preferred embodiments, this hydrolysis is effected with aqueous methanolic potassium carbonate, at reflux temperature for about 30 mintues.

An alternative method for preparing the compounds of this invention is set forth in Reaction Sequence 2.

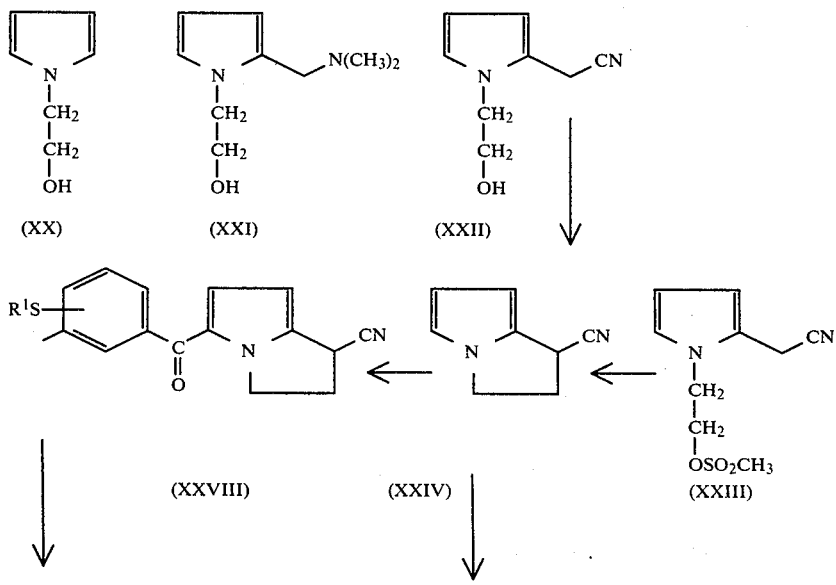

REACTION SEQUENCE 2

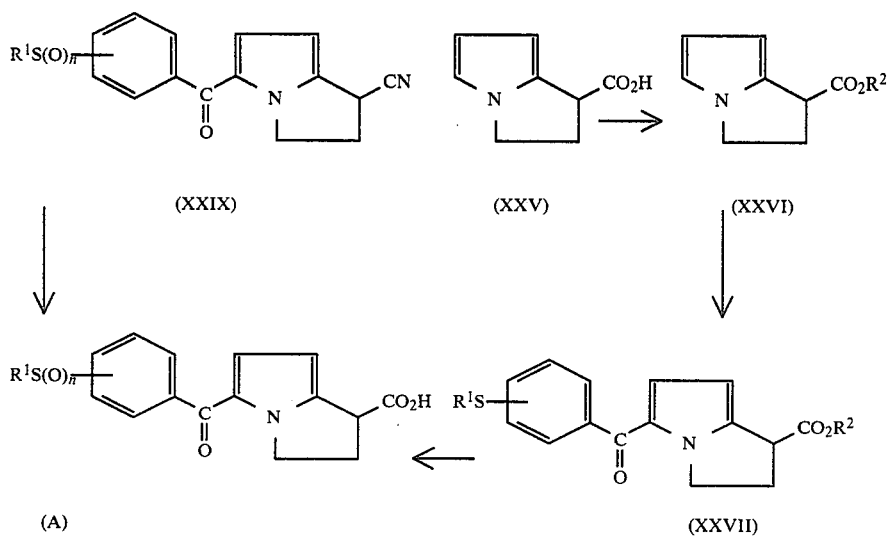

The starting compound 2-aminoethanol acetate is prepared by reacting 2-aminoethanol with glacial acetic acid at a temperature of between 5° and 50° C. This compound is then reacted with dimethoxytetrahydrofuran at reflux temperature for a period of time sufficient to give the desired pyrrole represented by Formula (XX) and the corresponding acetate. This is generally less than about 5 hours. After extracting the product from the reaction mixture, this mixture is hydrolyzed using a basic alcohol mixture such as sodium hydroxide and methanol at room temperature to give the desired product represented by Formula (XX).

This in turn is reacted at slightly elevated temperatures, e.g. 20°–60° C., with a solution of dimethylamine hydrochloride in aqueous formaldehyde to give 1-(2-hydroxyethyl)-2-dimethylaminomethylpyrrole. After extraction with a suitable organic solvent such as dichloromethane and subsequent purification by evaporation and distillation, the compound represented by Formula (XXI) is then dissolved in acetone and is maintained in an inert atmosphere using nitrogen or argon and a slight molar excess of dimethylsulfate is added to the cooled reaction mixture at such a rate that the temperature does not exceed about 5° C. When addition of the dimethylsulfate is completed, the solution is stirred at room temperature and a solution of sodium cyanide in water is added. The resulting reaction mixture is heated to reflux temperature, i.e. generally about 90°–100° C. and the distillate is collected. The reaction mixture is heated at a gentle reflux for a suitable period of time, generally less than 2 hours, preferably about ½ hour and water is added to the mixture. After extracting, drying and purification by column chromatography, a nitrile represented by Formula (XXII) is obtained, namely 1-(2-hydroxyethyl)pyrrol-2-yl-acetonitrile.

The compound of Formula (XXII) is then converted to the corresponding 1-(2-methanesulfonyloxy)ethyl-pyrrol-2-yl-acetonitrile by following procedures which are well known in the art and discussed hereinbefore in the discussion of the preparation of the compound represented by Formula (V) from the compound represented by Formula (IV) in Reaction Sequence 1. The mesyl ester represented by Formula (XXIII) is converted to the corresponding 1-cyano-1,2-dihydro-3H-pyrrolo[1,2-a]pyrrole of Formula (XXIV) according to procedures set forth hereinbefore in the discussion of Reaction Sequence 1 in the conversion of the compound of Formula (V) to the compound of Formula (VII). The preparation of this compound is also discussed in U.S. Pat. No. 4,140,698 to Van Horn et al. That patent is incorporated herein by reference.

In Reaction Sequence 2, the key intermediate is the nitrile represented by Formula (XXIV). This nitrile can be converted into the acid represented by Formula (XXV) by reacting with aqueous sodium or potassium hydroxide in ethylene glycol at elevated temperatures of up to 120° C. for a time sufficient for the reaction to take place, generally less than about 5 hours. Extracting the reaction mixture with a suitable organic solvent and bringing the aqueous phase to an acid pH using concentrated hydrochloric acid and extracting from water results in the acid represented by Formula (XXV). This in turn is converted to the ester of Formula (XXVI) by reaction with a lower aliphatic alcohol in the presence of an acid such as hydrochloric acid as set forth in the discussion of Reaction Sequence 1 in the converstion of a compound of Formula (VIII) to one of Formula (IX).

A compound of Formula (XXVI) is then converted to the alkylthiobenzoyl compound of Formula (XXVII) which in turn is converted to the oxidized form (A) according to procedures discussed hereinbefore relating to the conversion of compounds of Formulas (X) to (XI) and (XI) to (A) in Reaction Sequence 1.

Alternately, the intermediate nitrile of Formula (XXIV) can be converted into the nitriles of Formulas (XXVIII) and (XXIX) in Reaction Sequence 2 using reaction conditions discussed hereinbefore in the conversion of the compound of Formulas (X) to (XI) and (XII) in Reaction Sequence 1. The compound of Formula (XXIX), in turn, is converted to a compound of the invention (A) by converting the nitrile moiety to an acid as discussed hereinbefore.

The compounds of Formula (A) can be resolved, according to methods known in the art, to obtain the corresponding individual isomers thereof.

The (l)-acid isomers and (d)-acid isomers of the compounds of Formula (A) can be obtained by applying the known technique of high pressure liquid chromotography (HPLC) to the α-phenethyl diastereoisomeric esters of the compounds of Formula (A), followed by acid cleavage. Thus, for example, the compounds of Formula (A) wherein R and $R^1$ are both hydrogen can be subjected to further treatment in accordance with the following flow diagram:

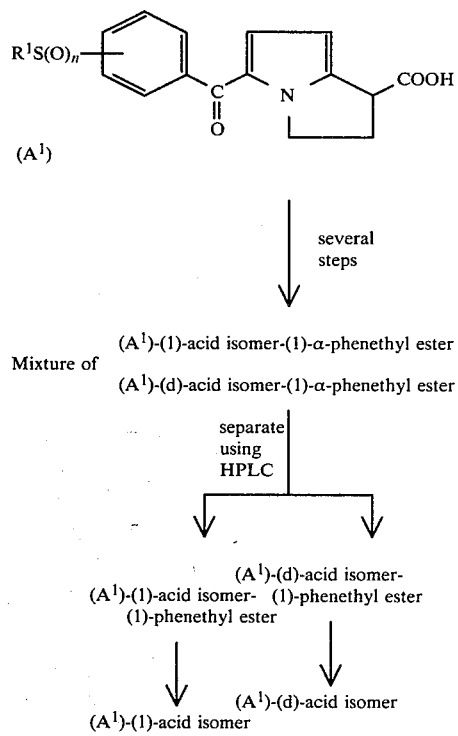

The free acids of Formula (A) can be converted into other alkyl esters having from 1 to 12 carbon atoms by conventional methods, e.g., by treatment with (a) the alcohol corresponding to the desired ester in the presence of a strong mineral acid, (b) an etheral diazoalkane or (c) the desired alkyl iodide in the presence of lithium carbonate.

The salt derivatives of the compounds of Formula (A) are prepared by treating these free acids with an appropriate amount of a pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purine, piperazine, piperidine, N-ethylpiperidine, polyamine resins and the like. The reaction is conducted in water, alone or in combination with an inert, water-misible organic solvent, at a temperature of from about 0° to about 100° C., preferably at room temperature. Typical inert, water-miscible organic solvents include methanol, ethanol, isopropanol, butanol, acetone, dioxane or tetrahydrofuran. The molar ratio of compounds of Formula (A) to base used are chosen to provide the ratio desired for any particular salt. For preparing, for example, the calcium salts or magnesium salts of the compounds of Formula (A), the free acid starting material can be treated with at least one-half molar equivalent of pharmaceutically acceptable base to yield a neutral salt. When the aluminum salts of the compounds of Formula (A) are prepared, at least one-third molar equivalent of the pharmaceutically acceptable base are employed if a neutral salt product is desired.

In the preferred procedure, the calcium salts and magnesium salts of the compounds of Formula (A) can be prepared by treating the corresponding sodium or potassium salts thereof with at least one-half molar equivalent of calcium chloride or magnesium chloride, respectively, in an aqueous solution, alone or in combination with an inert water-miscible organic solvent, at a temperature of from about 20° to about 100° C. Preferably, the aluminum salts of the compounds hereof, can be prepared by treating the corresponding free acids with at least one-third molar equivalent of an aluminum alkoxide, such as aluminum triethoxide, aluminum tripropoxide and the like, in a hydrocarbon solvent, such as benzene, xylene, cyclohexane and the like, at a temperature of from about 20° to about 115° C. Similar procedures can be used to prepare salts of inorganic bases which are not sufficiently soluble for easy reaction.

It is to be understood that isolation of the compounds described herein can be effected, if desired, by any suitable separation or purification procedure, such as for example, extraction, filtration, evaporation, distillation, crystallization, thin-layer chromatography or column chromatography, high pressure liquid chromotography (HPLC) or a combination of these procedures.

UTILITY AND ADMINISTRATION

The compounds of Formula (A) and the pharmaceutically acceptable non-toxic esters and salts thereof, are useful as anti-inflammatory agents, analgetic agents, platelet aggregation inhibitors, fibrinolytic agents, and as smooth muscle relaxants. These compounds can be used both prophylactically and therapeutically.

The compositions containing these compounds are thus useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the instant compounds are useful for the relief of these conditions as well as the inflammation.

Administration of the active compounds of Formula (A) and the pharmaceutically acceptable, non-toxic esters and salts thereof, in an appropriate pharmaceutical composition can be via any of the accepted modes of administration of agents for the treatment of inflammation, pain or pyrexia, or the prophylaxis thereof. Thus, administration can be for example, orally, parenterally or topically, in the form of solid, semi-solid or liquid dosage forms, such as, for example, tablets, suppositories, pills, capsules, powders, solutions, suspensions, emulsions, creams, lotions, ointments or the like preferably in unit dosage forms suitable for simple administration of precise dosages. The compositions will include a conventional pharmaceutical carrier or excipient and an active compound of Formula (A) and the pharmaceutically acceptable non-toxic esters and salts thereof, and, in addition, may include other medicinal agents, pharmaceutical agents, carriers, adjuvants, etc.

The preferred manner of administration, for the conditions detailed above, is oral using a convenient daily dosage regimen which can be adjusted according to the degree of affliction. Generally, a daily dose of from 25 to 500 mg. of the active compound of Formula (A) and the pharmaceutically acceptable, non-toxic esters and salts thereof is used. Most conditions respond to treatment comprising a dosage level of the order of 0.5 to 6 mg. per kilogram of body weight per day. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccarine, talcum, cellulose, glucose, gelatin, sucrose, magnesium carbonate, and the like. Such compositions take the form of solutions, suspensions, tablests, pills, capsules, powders, sustained release formulations and the like.

The active compounds of Formula (A) and the pharmaceutically acceptable, non-toxic esters and salts thereof, may be formulated into a suppositiory using, for example, polyalkylene glycols, for example, polypropylene glycol, as the carrier. Liquid pharmaceutically administerable compositions can, for example, be prepared by dissolving, dispersing, etc. an active compound, as described above, and optional pharmaceutical adjuvants in a carrier, such as, for example, water, saline, aqueous dextrose, glycerol, ethanol and the like, to thereby form a solution or suspension. If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's Pharmaceutical Sciences, Mack Publishing Company, Easton, Pennsylvania, 15th Edition, 1975. The composition to be administered will, in any event, contain a quantity of the active compounds(s) in a pharmaceutically effective amount for relief of the particular condition being treated in accordance with the teachings of this invention.

The compounds of Formula (A) and the non-toxic, pharmaceutically acceptable esters and salts thereof, described above, are also uterine smooth muscle relaxants and thus are useful as agents for maintaining the pregnancy of pregnant mammals, for the benefit of the mother and/or fetus, until termination of the pregnancy is considered, from a medical point of view, to be favorable, or more favorable, for the mother and/or the fetus. It should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged", a factor which may be advantageious to either the mother and/or the fetus.

In particular, the compounds of Formula (A) and the pharmaceutically acceptable, non-toxic esters and salts thereof, are used as agents for delaying the onset of, or for postponing, parturition. As used in this application, the phrase "to delay the onset of parturition" is intended to cover that delay in parturition caused by the administration of the compounds of Formula (A) and the pharmaceutically acceptable, non-toxic esters and salts thereof, at any time before uterin muscle contractions have begun. Thus, it is intended that the aforementioned phrase cover abortion prevention early in pregnancy (i.e., before the fetus is "viable") as well as delaying premature parturition, a term which sometimes is used with reference to that premature labor experienced later in the pregnancy when the fetus is considered to be "viable". In either case, the agents are administered as prophylactic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications that the preganancy might be terminated prior to that time and is considered favorable to the mother and/or fetus.

With respect to animals, this treatment can also be utilized to synchronize the deliveries from a group of pregnant animals to happen at or about the same time, or to happen at or about a desired time and/or place, when the births can be handled with greater facility.

As used in this application, the phrase "postponing parturition" is intended to cover that delay in parturition caused by the administration of the compounds of Formula (A) and the pharmaceutically acceptable, non-toxic esters and salts thereof after uterine muscle contractions have begun. The condition of the patient, including the time within the gestation period when the contractions have begun, the severity of the contractions and how long the contractions have taken place will affect the results achieved with the administration of the compounds hereof. For example, the effect can be to reduce the intensity and/or the duration of the contractions (the actual act of parturition being "prolonged"), or to stop the contractions altogether. In either case, the effect will be to prolong the gestation period although, depending upon the conditions of the patient as described above, the effect may either be slight or, under appropriate circumstances, somewhat greater. Such administration may be to prevent spontaneous abortion, to cause the delivery to be more easily accomplished and/or less painful to the mother, or to occur at a more appropriate time and/or place.

In all cases, administration of the compounds of Formula (A) and the pharmaceutically acceptable, non-toxic esters and salts thereof, for the purposes set forth herein should be consistent with best and/or accepted medical (or veterinary) practices so as to maximize the benefits to the mother and the fetus. For example, administration should not be continued so long past full term that the fetus dies in utero.

In the practice of the methods of the present invention relating to the treatment of pregnant mammals, a therapeutically effective amount of compounds of Formula (A) and the pharmaceutically acceptable, non-toxic esters and salts thereof, or a pharmaceutical composition containing same, is administered to the pregnant mammal via any of the usual and acceptable methods known in the art. The compound can be administered either singly or in combination with another compound or compounds, as defined above, or other pharmaceutical agents, carriers, adjuvants, etc. Such compound(s) or compositions can be administered orally, parenterally, either in the form of solid, semi-solid, or liquid dosage forms. Typically, administration is by a pharmaceutical composition containing the pharmaceutically active compound and one or more pharmaceutical carriers or adjuvants.

The administerable pharmaceutical composition may take the form of oral tablets, vaginal or uterine tablets or suppositories, pills, capsules, liquid solutions, suspensions, or the like, preferably in unit dosage forms suitable for simple administration of precise dosages. Conventional non-toxic solid carriers include, for example, pharmaceutical grades of mannitol, lactose, starch, magnesium stearate, sodium saccharin, talcum, cellulose, glucose, gelatin, sucrose, magnesium carbonate, and the like. The active compound as defined above may be formulated as suppositories using, for example, polyalkylene glycols, for example, polypropylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension, if desired, the pharmaceutical composition to administer may also contain minor amounts of non-toxic auxiliary substances such as wetting or emulsifying agents, pH buffering agents and the like, for example, sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pennsylvania., 15th Edition, 1975. The composition or formulation to be administered will, in any event, contain a quantity of the active compound(s) in an amount effective to delay the onset of parturition or to postpone parturition if uterine contractions have already begun. Generally a daily dose of from 0.5 to about 25 mg. of the active compound per kilogram of body weight will be administered, with administration being a single daily dose or up to three or four smaller dosages regularly given throughout the day. The amount of active compound administered will, of course, depend on its relative activity.

The following Preparations and Examples illustrate the invention but are not intended to limit its scope. The abbreviation t.l.c. refers to thin-layer chromatography and all mixture ratios used with regard to liquids refer to volume ratios. Also where necessary, examples are repeated to prepare additional material for subsequent examples; and unless otherwise specified the reactions are carried out at room temperature (20° to 30° C.).

PREPARATION 1

Alkyl 1,2-dihydro-3H-pyrrolo[1,2-a]pyrrole-1-carboxylates

A. A 250 ml. 3-necked round bottomed flask containing a magnetic stirring bar and fitted with a calcium chloride filled drying tube is connected directly (via one of the outer necks) by means of a receiver adapter and short (3-inch) water condenser to the acetal pyrolysis apparatus. This latter apparatus consists of a 100 ml round bottomed flask [previously charged with 15.6 g. of oxalic acid dihydrate and 11.82 g of bromoacetaldehyde diethyl acetal, prepared from vinyl acetate, as described by P. Z. Bedoukian, J. Am. Chem. Soc. 66, 651 (1944)], topped with a 6-inch Vigreux column, bearing a thermometer, connected to the above mentioned condenser.

The three-necked flask is charged with 3.36 g of ethanolamine cooled in an ice bath at 0°–10° C. and treated dropwise, with stirring, with 8.7 g of dimethyl 1,3-acetonedicarboxylate. Methyl 3-carbomethoxymethyl-2(2'-hydroxyethyl)amino acrylate (III) forms immediately. When the addition is completed, the ice bath is removed and 100 ml of dry acetonitrile is added. The pyrolysis part of the apparatus is placed in an oil bath and the temperature thereof is raised to 150°–160° C. The bromoacetaldehyde solution which forms is distilled (b.p. 80°–83° C./580 mm) directly into the magnetically stirred solution of the vinylamine (III). When the distillation temperature drops below 80° C., the pyrolysis apparatus is disconnected and replaced by a reflux condenser fitted with a drying tube containing calcium chloride. The solution is heated at reflux temperature for 1 hour, the solvent is removed under reduced pressure and then 200 ml of methanol and 20 g of silica gel are added to the residue. This mixture is evaporated to dryness in vacuum and placed on top of a column of 200 g of silica gel packed in hexane. The column is then eluted with hexane:ethyl actate (80:20; 500 ml) and hexane:ethyl acetate (1:1; 9×500 ml). Fractions 2 and 3 contain less polar impurities and dimethyl 1,3-acetonedicarboxylate; fractions 4–8 afford 4.1 g of methyl N-(2-hydroxyethyl)-3-carbomethoxypyrrole-2-acetate (IV,R=H), which upon recrystallization from ether-hexane has a melting point of 52°–54° C.

B. To a stirred solution of 4.1 g of methyl N-(2-hydroxyethyl)-3-carbomethoxypyrrole-2-acetate in 35 ml of dry dichloromethane cooled to −10° C., are added 2.65 ml of triethylamine and thereafter, in a dropwise fashion, 1.46 ml of methanesulfonyl chloride, maintaining the temperature of the reaction mixture at −10° to −5° C. The course of the reaction is followed by t.l.c. analysis using chloroform:acetone (90:10). When the reaction appears to be complete (about 30 minutes after the addition of the methanesulfonyl chloride is terminated) there is added slowly 10 ml of water. The organic phase is separated, washed with water (3×30 ml), dried over sodium sulfate and evaporated under reduced pressure. Crystallization of the residue from dichloromethane affords 4.75 g (77.7%) of methyl N-(2-mesyloxyethyl)-3-carbomethoxypyrrole-2-acetate (V,R=H), m.p. 99°–101° C.

C. A solution of 785 mg of methyl N-(2-mesyloxyethyl)-3-carbomethoxypyrrole-2-acetate and 1.83 g of sodium iodide in 10 ml of acetonitrile is refluxed for 1 hour. The cooled reaction mixture is evaporated to dryness under reduced pressure and the residue is triturated with water. The insoluble material is separated by filtration and is air dried, thus obtaining 840 mg (97%) of methyl N-(2-iodoethyl)-3-carbomethoxypyrrole-2-acetate (VI, R=H), m.p. 137°–138° C.

D. A solution of 1 g of methyl N-(2-iodoethyl)-3-carbomethoxypyrrole-2-acetate in 5 ml of dry dimethylformamide is stirred, under an atmosphere of argon, with 137 mg of 50% sodium hydride in mineral oil. The reaction mixture is maintained for 20 minutes at room temperature and then quenched with 100 ml of water. The product is extracted with ethyl acetate (3×50 ml), the combined extracts are washed with water, dried over magnesium sulfate and evaporated to dryness. Chromatography of the residue on 20 g of silica gel using hexane:ethyl acetate (4:1) as eluant, affords 500 mg (80%) of dimethyl 1,2-dihydro-3H-pyrrolo-[1,2-a]pyrrole-1,7-dicarboxylate (VII, R=H) m.p. 70°-71° C.

A solution of 1.80 g of dimethyl 1,2-dihydro-3H-pyrrolo[1,2-a]pyrrole-1,7-dicarboxylate in 20 ml of methanol is treated with a solution of 4.48 g of potassium hydroxide in 20 ml of water, and the reaction mixture is refluxed for 6 hours. The cooled solution is evaporated to dryness and the residue is treated with 50 ml of saturated sodium chloride solution. The resultant solution is acidified with 6 N hydroxhloric acid and extracted with ethyl acetate (3×50 ml). The combined extracts are dried over magnesium sulfate and evaporated to dryness under reduced pressure, to yield 1.51 g (95%) of 1,2-dihydro-2H-pyrrolo[1,2-a]pyrrole-1,7-dicarboxylic acid (VIII, R=H), m.p. 220° C., with decomposition.

E. A solution of 1.34 g of 1,2-dihydro-3H-pyrrolo[1,2-a]pyrrole-1,7-dicarboxylic acid in 50 ml of isopropanol, cooled in an ice bath is saturated with gaseous hydrogen chloride, maintaining the temperature of the reaction mixture below 50° C. The ice bath is then removed and the reaction mixture is stirred for 1.5 hours at room temperature, and evaporated to dryness under reduced pressure; 10 ml of benzene is added to the residue and the solution is evaporated under vacuum once again, repeating this process a total of three times to completely remove the excess hydrogen chloride, thus obtaining 1.58 g (96%) of a product which upon crystallization from methanol-ethyl acetate gives isopropyl 1,2-dihydro-3H-pyrrolo[1,2-a]pyrrole-1-carboxylate-7-carboxylic acid (IX, R=H, $R^2=iC_3H_7$), m.p. 144°-145° C.

In a similar manner but substituting methanol, ethanol, propanol and n-butanol for isopropanol in the above procedure there are respectively obtained:
  methyl 1,2-dihydro-3H-pyrrolo[1,2-a]pyrrole-1-carboxylate-7-carboxylic acid,
  ethyl 1,2-dihydro-3H-pyrrolo[1,2-a]pyrrole-1-carboxylate-7-carboxylic acid,
  propyl 1,2-dihydro-3H-pyrrolo[1,2-a]pyrrole-1-carboxylate-7-carboxylic acid, and
  butyl 1,2-dihydro-3H-pyrrolo[1,2-a]pyrrole-1-carboxylate-7-carboxylic acid.

F. 1.054 G. of isopropyl 1,2-dihydro-3H-pyrrolo[1,2-a]pyrrole-1-carboxylate-7-carboxylic acid is heated to 240°-250° C. in a dry 10 ml round bottomed flask, distilling directly the reaction product from the reaction vessel. In this manner there is obtained 745 mg (87%) of isopropyl-1,2-dihydro-3H-pyrrolo[1,2-a]pyrrole-1-carboxylate (X, R=H, $R^2=iC_3H_7$), a pale yellow oil, having the following physical constants: U.V.: λmax $^{MeOH}$ 215 nm (ε6020); I.R.: νmax $^{CHCl_3}$ 1725 cm$^{-1}$, N.M.R.; δTMS $_{CDCl_3}$ 1.22 (d,J=7 Hz, 6H), 2.40-2.90 (m, 2H), 2.60-4.20 (m, 2H), 3.60-4.20 (m, 2H), 4.65-5.2 (m, 1H), 5.73-5.92 (m, 1H), 6.10 (t,J=3 Hz, 1H), 6.43-6.53 ppm. (m, 1H).

In a similar manner by heating the other alkyl 1,2-dihydro-3H-pyrrolo[1,2-a]pyrrole-1-carboxylate-7-carboxylic acids of Part E of this preparation, the following compounds are prepared:
  methyl 1,2-dihydro-3H-pyrrolo[1,2-a]pyrrole-1-carboxylate,
  ethyl 1,2-dihydro-3H-pyrrolo[1,2-a]pyrrole-1-carboxylate,
  propyl 1,2-dihydro-3H-pyrrolo[1,2-a]pyrrole-1-carboxylate, and
  butyl 1,2-dihydro-3H-pyrrolo[1,2-a]pyrrole-1-carboxylate.

PREPARATION 2

Alkylthiobenzoyl chlorides

A. A mixture of 56 mmol (8.85 g) p-methylthiobenzoic acid, 40 ml benzene and 112 mmol (7.4 ml) thionyl chloride is boiled under reflux for 24 hours. The benzene and excess thionyl chloride are removed under vacuum to give p-methylthiobenzoyl chloride mp 48-52 in 80% yield.

B. In a similar manner, by following the procedure of Part A of this preparation, but substituting other suitable alkylthiobenzoic acids for p-methylthiobenzoic acid, other acid chlorides are prepared such as
  o-methylthiobenzoyl chloride;
  m-methylthiobenzoyl chloride;
  o-ethylthiobenzoyl chloride;
  m-ethylthiobenzoyl chloride;
  p-ethylthiobenzoyl chloride;
  p-propylthiobenzoyl chloride;
  o-isopropylthiobenzoyl chloride;
  m-isopropylthiobenzoyl chloride;
  p-butylthiobenzoyl chloride;
  o-isobutylthiobenzoyl chloride;
  m-isobutylthiobenzoyl chloride;
  m-isobutylthiobenzoyl chloride;
  m-(t-butylthio)benzoyl chloride; and
  p-(t-butylthio)benzoyl chloride.

PREPARATION 3

Alkyl-5-alkylthiobenzoyl-1,2-dihydro-3H-pyrrolo[1,2-a]pyrrole-1-carboxylates

A. A solution of 15 mmol (2.8 g) of p-methylthiobenzoyl chloride and 5 mmol (0.826 g) of methyl 1,2-dihydro-3H-pyrrolo[1,2-a]pyrrole-1-carboxylate in 50 ml of anhydrous toluene is boiled under reflux, in a nitrogen atmosphere, until t.l.c. indicated there is no more starting material present (about one hour). The solution is cooled and the solvent evaporated under vacuum. The crude product is then purified by column chromatography on a 500 g column of silica gel using hexane-ethyl acetate (3:2) to elute the product. Removal of the solvent under vacuum and crystallization from methylene dichloride-ethyl ether gave methyl 5-(p-methylthio)benzoyl-1,2-dihydro-3H-pyrrolo[1,2-a]pyrrole-1-carboxylate, m.p. 77°-78° C.

B. In a similar manner, by following the procedure of Part A of this example but substituting other suitable alkylthiobenzoyl chlorides set forth hereinbefore in Preparation 2, Part B for p-methylthiobenzoyl chloride, other compounds useful as intermediates to compounds of this invention are prepared such as
  methyl 5-(o-methylthio)benzoyl-1,2-dihydro-3H-pyrrolo[1,2-a]pyrrole-1-carboxylate;
  methyl 5-(m-methylthio)benzoyl-1,2-dihydro-3H-pyrrolo[1,2-a]pyrrole-1-carboxylate;
  methyl 5-(o-ethylthio)benzoyl-1,2-dihydro-3H-pyrrolo[1,2-a]pyrrole-1-carboxylate;
  methyl 5-(m-ethylthio)benzoyl-1,2-dihydro-3H-pyrrolo[1,2-a]pyrrole-1-carboxylate;
  methyl 5-(p-ethylthio)benzoyl-1,2-dihydro-3H-pyrrolo[1,2-a]pyrrole-1-carboxylate;
  methyl 5-(p-propylthio)benzoyl-1,2-dihydro-3H-pyrrolo[1,2-a]pyrrole-1-carboxylate;

methyl 5-(o-isopropylthio)benzoyl-1,2-dihydro-3H-pyrrolo[1,2-a]pyrrole-1-carboxylate;

methyl 5-(m-isopropylthio)benzoyl-1,2-dihydro-3H-pyrrolo[1,2-a]pyrrole-1-carboxylate;

methyl 5-(p-butylthio)benzoyl-1,2-dihydro-3H-pyrrolo[1,2-a]pyrrole-1-carboxylate;

methyl 5-(o-isobutylthio)benzoyl-1,2-dihydro-3H-pyrrolo[1,2-a]pyrrole-1-carboxylate;

methyl 5-(m-isobutylthio)benzoyl-1,2-dihydro-3H-pyrrolo[1,2-a]pyrrole-1-carboxylate;

methyl 5-(p-isobutylthio)benzoyl-1,2-dihydro-3H-pyrrolo[1,2-a]pyrrole-1-carboxylate;

methyl 5-[m-(t-butylthio)]benzoyl-1,2-dihydro-3H-pyrrolo[1,2-a]pyrrole-1-carboxylate; and methyl 5-[p-(t-butylthio)]benzoyl-1,2-dihydro-3H-pyrrolo[1,2-a]pyrrole-1-carboxylate.

C. In a similar manner, by following the procedure of Part A of this example, but substitutuing other suitable alkyl 1,2-dihydro-3H-pyrrolo[1,2-a]pyrrole-1-carboxylates of Preparation 1, for methyl 5-(p-methylthiobenzoyl-1,2-dihydro-3H-pyrrolo[1,2-a]pyrrole-1-carboxylate other intermediates are obtained such as ethyl 5-(p-methylthio)benzoyl-1,2-dihydro-3H-pyrrolo[1,2-a]pyrrole-1-carboxylate;

propyl 5-(p-methylthio)benzoyl-1,2-dihydro-3H-pyrrolo[1,2-a]pyrrole-1-carboxylate;

isopropyl 5-(p-methylthio)benzoyl-1,2-dihydro-3H-pyrrolo[1,2-a]pyrrole-1-carboxylate;

butyl 5-(p-methylthio)benzoyl-1,2-dihydro-3H-pyrrolo[1,2-a]pyrrole-1-carboxylate;

isobutyl 5-(p-methylthio)benzoyl-1,2-dihydro-3H-pyrrolo[1,2-a]pyrrole-1-carboxylate;

t-butyl 5-(p-methylthio)benzoyl-1,2-dihydro-3H-pyrrolo[1,2-a]pyrrole-1-carboxylate; and the analogous lower alkyl esters of the compounds of Part B of this example.

PREPARATION 4

5-Alkylthiobenzoyl-1,2-dihydro-3H-pyrrolo[1,2-a]-pyrrole-1-carboxylic acids

A. A mixture of 6.9 mmol (2.17 g) methyl 5-(p-methylthio)benzoyl-1,2-dihydro-3H-pyrrolo[1,2-a]pyrrole-1-carboxylate, 13.8 mmol (1.91 g) potassium carbonate, 40 ml methanol and 10 ml water is refluxed for 15 minutes in a nitrogen atmosphere. The mixture is cooled to ambient temperature and the methanol removed under vacuum. The residue is dissolved in 50 ml water and the resulting solution is washed three times with 30 ml ethyl acetate, acidified with 28 mmol (3.55 g) oxalic acid, saturated with sodium chloride, then extracted with 50 ml ethyl acetate ten times. The extract is dried over sodium sulfate and the ethyl acetate is removed under vacuum to give a crystalline residue. Crystallization from an ethyl acetate-ethyl ether mixture gives 5-(p-methylthio)-benzoyl-1,2-dihydro-3H-pyrrolo[1,2-a]pyrrole-1-carboxylic acid, m.p. 156°–157° C.

B. Similarly, by following in principle the procedure of Part A of this example but substituting other alkyl 5-alkylthiobenzoyl-1,2-dihydro-3H-pyrrolo[1,2-a]pyrrole-1-carboxylate made according to Example 1, Part B for methyl 5-(p-methylthio)benzoyl-1,2-dihydro-3H-pyrrolo[1,2-a]pyrrole-1-carboxylic acid, other carboxylic acids are prepared such as 5-(o-methylthio)benzoyl-1,2-dihydro-3H-pyrrolo[1,2-a]pyrrole-1-carboxylic acid;

5-(m-methylthio)benzoyl-1,2-dihydro-3H-pyrrolo[1,2-a]pyrrole-1-carboxylic acid;

5-(o-ethylthio)benzoyl-1,2-dihydro-3H-pyrrolo[1,2-a]pyrrole-1-carboxylic acid;

5-(m-ethylthio)benzoyl-1,2-dihydro-3H-pyrrolo[1,2-a]pyrrole-1-carboxylic acid;

5-(p-ethylthio)benzoyl-1,2-dihydro-3H-pyrrolo[1,2-a]pyrrole-1-carboxylic acid;

5-(p-propylthio)benzoyl-1,2-dihydro-3H-pyrrolo[1,2-a]pyrrole-1-carboxylic acid;

5-(o-isopropylthio)benzoyl-1,2-dihydro-3H-pyrrolo[1,2-a]pyrrole-1-carboxylic acid;

5-(m-isopropylthio)benzoyl-1,2-dihydro-3H-pyrrolo[1,2-a]pyrrole-1-carboxylic acid;

5-(p-butylthio)benzoyl-1,2-dihydro-3H-pyrrolo[1,2-a]pyrrole-1-carboxylic acid;

5-(o-isobutylthio)benzoyl-1,2-dihydro-3H-pyrrolo[1,2-a]pyrrole-1-carboxylic acid;

5-(m-isobutylthio)benzoyl-1,2-dihydro-3H-pyrrolo[1,2-a]pyrrole-1-carboxylic acid;

5-(p-isobutylthio)benzoyl-1,2-dihydro-3H-pyrrolo[1,2-a]pyrrole-1-carboxylic acid;

5-[m-(t-butylthio)]benzoyl-1,2-dihydro-3H-pyrrolo[1,2-a]pyrrole-1-carboxylic acid; and 5-[p-(t-butylthio)]benzoyl-1,2-dihydro-3H-pyrrolo[1,2-a]pyrrole-1-carboxylic acid.

PREPARATION 5

A solution of 215 mg of N,N-dimethyl-p-methylthiobenzamide and 0.11 of phosphorus oxychloride in 2 ml of 1,2-dichloroethane is refluxed for 30 minutes. To this solution is added a solution of 193 mg of methyl 1,2-dihydro-3H-pyrrolo[1,2-a]pyrrole-1-carboxylate in 2 ml of 1,2-dichloroethane. The reaction mixture is refluxed under an argon atmosphere for 8 hours, treated with 405 mg of sodium acetate and refluxed for a further 5 hours. The resultant mixture is then evaporated to dryness and the residue is chromatographed on 12 g of silica gel, eluting with hexane:ethyl acetate (3:1), thus obtaining methyl 5-(p-methylthio)benzoyl-1,2-dihydro-3H-pyrrolo[1,2-a]pyrrole-1-carboxylate (XI, R=H, $R^1$=CH$_3$, $R^2$=CH$_3$).

Following this procedure using 1.1 to 5 molar equivalents of,

N,N-dimethyl-o-methylthiobenzamide;
N,N-dimethyl-m-methylthiobenzamide;
N,N-dimethyl-o-ethylthiobenzamide;
N,N-dimethyl-m-ethylthiobenzamide;
N,N-dimethyl-p-ethylthiobenzamide;
N,N-dimethyl-p-propylthiobenzamide;
N,N-dimethyl-o-isopropylthiobenzamide;
N,N-dimethyl-m-isopropylthiobenzamide;
N,N-dimethyl-p-butylthiobenzamide;
N,N-dimethyl-o-isobutylthiobenzamide;
N,N-dimethyl-m-isobutylthiobenzamide;
N,N-dimethyl-p-isobutylthiobenzamide;
N,N-dimethyl-m-(t-butylthio)benzamide; and
N,N-dimethyl-p-(t-butylthio)benzamide, in place of N,N-dimethyl-p-methythiobenzamide, and monitoring the course of the reaction by t.l.c., there are obtained other intermediates to compounds of the invention as set forth in Preparation 3.

PREPARATION 6

A. To a mixture of 8.21 g of formaldehyde solution (37% aqueous) and 8.84 g of dimethylamine hydrochloride there is added 11.5 g of N-hydroxyethylpyrrole (see Shun-Ichi Murahashi et al., J.C.S. Chem Comm., 1974, 931–932) over a period of about 8 minutes whilst agitating and keeping the temperature below 60° C., with cooling if necessary. The temperature is permitted to drop to room temperature for 15 hours, followed by the addition of 16 ml of 25% aqueous sodium hydroxide solution, agitation for 5 minutes, and the addition of 19 ml of methylene chloride. The organic portions are combined and washed with a mixture of 11 ml of saturated aqueous sodium chloride solution and 8 ml of water. The washed organic layer is dried over anhydrous sodium sulfate and the solvent is removed under vacuum to yield 17.2 g of an orange-yellow oil which, upon purification on a silica gel chromatography column (using 10% methanol in methylene chloride as solvent) yielded 12.9 g of 1-hydroxyethyl-2-[(N,N-dimethylamino)methyl]-pyrrole, having the following analysis:

Calculated: C, 64.25%; H, 9.59%; N, 16.65%. Found: C, 63.39%; H, 10.14%; N, 16.46%.

B. To 100 ml of acetone there is added 21.5 g of 1-hydroxyethyl-2-[(N,N-dimethylamino)methyl]-pyrrole, and to this mixture at 0.° C., there is added 16.4 g of dimethylsufate, whilst keeping the temperature below 2° C. during the addition. The temperature is then permitted to rise to room temperature and the reaction mixture agitated at room temperature for one hour. The thus-obtained reaction mixture is then added to a hot (about 90° C.) solution of 12.6 g of sodium cyanide in 27 ml of water, the addition being at such a rate, while at the same time distilling the solvent off, that the internal reaction flask temperature is kept at about 90° C.–95° C. When the addition is complete, the mixture is brought to reflux and heated under reflux for 15 minutes. The mixture is cooled to 25° C., followed by the addition of 40 ml of water and 60 ml of methylene chloride. The organic layer is separated, washed with 30 ml of a mixture of 50:50 saturated aqueous sodium chloride:water, the water layer is extracted twice with 30 ml of methylene chlkoride, and the combined organic layers are dried over anhydrous sodium sulfate and the solvent removed under vacuum to yield 21 g of a brown oil which upon purification on a silica gel chromatography column (using 50:50-ethyl acetate:hexane as solvent) yields 13 g of 1-hydroxyethylpyrrole-2-acetonitrile having the following analysis:

Calculated: C, 63.98%; H, 6.71%; N, 18.66%. Found: C, 63.91%; H, 6.76%; N, 18.91%.

C. 1.6 G of 1-hydroxyethylpyrrole-2-acetonitrile is charged to a mixture of 12 ml of methylene chloride and 1.3 g of triethylamine, the flask being purged with nitrogen and the contents thereof being cooled to −10° C. 1.34 G of methanesulfonyl chloride is then added, whilst maintaining the temperature below 0° C., for 15 minutes. To the reaction mixture is added 10 ml of a mixture of 50:50-saturated aqueous sodium chloride soltuion:water, followed by extracting four times with 15 ml portions of methylene chloride and washing with dilute aqeuous sodium chloride solution, drying over anhydrous sodium sulfate and removing the solvent under vacuum to yield 2.52 g of crude 1-(2-methanesulfonylethane)pyrrol-2-acetonitrile which is added to a mixture of 35 ml of acetonitrile and 3.76 g sodium iodide. The thus-obtained mixture is heated to 77° C. for one hour, cooled to 25° C., and 15 ml of methylene chloride is added thereto. The organic salts are filtered off and washed with methylene chloride. The solvent is removed from the filtrate under vacuum, leaving a residue which is taken up in a mixture of 30 ml of methylene chloride and 30 ml of dilute aqueous sodium chloride solution. The organic layer obtained is dried over anhydrous sodium sulfate and the solvent removed under vacuum to yield 2.85 g of crude 1-(2-iodoethane)-pyrrol-2-acetonitrile. 2.7 G of this product is dissolved in 10 ml of dimethylformamide and added slowly to a suspension of 0.24 g of sodium hydride (obtained from 0.48 g of 50% oil dispersion) in 10 ml of dimethylformamide while the temperature is kept below 15° C. The reaction slurry, under a nitrogen atmosphere, is agitated for one hour at 20° C., followed by the addition of 35 ml of water and extracted with five 20 ml portions of diethyl ether. The organic extracts are combined and dried over sodium sulfate, followed by removal of the solvent at atmospheric pressure to yield 1.4 g of a brown oil which upon purification on a silica gel chromatography column (using 3:1-hexane:ethyl acetate as solvent) yields 1 g of 1,2-dihydro-3H-pyrrolo[1,2-a]pyrrole-1-nitrile having a melting point of 44°–45° C. (crystallized from ethanol) and the following analysis:

Calculated: C, 72.70%; H, 6.10%; N, 21.20%. Found: C, 72.72%; H, 6.25%; N, 21.17%.

EXAMPLE 1

Alkyl 5-(p-alkylsulfinyl)benzoyl-1,2-dihydro-3H-pyrrolo[1,2-a]pyrrole-1-carboxylates A. A solution of 4.08 mmol. (0.703 g) of m-chloroperbenzoic acid in 20 ml chloroform is added over a 10 minute period to a solution of 3.74 mmol. (1.18 g) of methyl 5-(p-methylthio)benzoyl-1,2-dihydro-3H-pyrrolo[1,2-a]pyrrole-1-carboxylate in 100 ml of chloroform which has been cooled to 0° C. The mixture is stirred for 1 hour at 0° C. then is washed successively with 60 ml of sodium bicarbonate and two 20 ml portions of saturated sodium chloride solution. The organic phase is dried over sodium sulfate, the solvent is removed under vacuum and the residue is subjected to column chromatography on 350 g of silica gel eluting with ethyl acetate. Ethyl acetate is evaporated to give 0.944 g of a product in a 76% yield. Recrystallization of the product from a methylene chloride-ethyl ether mixture gives methyl 5-(p-methylsulfinyl)benzoyl-1,2-dihydro-3H-pyrrolo[1,2-a]pyrrole-1-carboxylate, m.p. of 113°–114° C.

B. In a similar manner, by following the procedure of Part A of this example but substituting other methyl 5-(p-alkylthio)benzoyl-1,2-dihydro-3H-pyrrolo[1,2-a]pyrrole-1-carboxylates for methyl 5-(p-methylthio)-benzoyl-1,2-dihydro-3H-pyrrolo[1,2-a]pyrrole-1-carboxylate, other compounds of the invention may be obtained such as methyl 5-(o-methylsulfinyl)benzoyl-1,2-dihydro-3H-pyrrolo[1,2-a]pyrrole-1-carboxylate;

methyl 5-(m-methylsulfinyl)benzoyl-1,2-dihydro-3H-pyrrolo[1,2-a]pyrrole-1-carboxylate;

methyl 5-(o-ethylsulfinyl)benzoyl-1,2-dihydro-3H-pyrrolo[1,2-a]pyrrole-1-carboxylate;

methyl 5-(m-ethylsulfinyl)benzoyl-1,2-dihydro-3H-pyrrolo[1,2-a]pyrrole-1-carboxylate;

methyl 5-(p-ethylsulfinyl)benzoyl-1,2-dihydro-3H-pyrrolo[1,2-a]pyrrole-1-carboxylate;

methyl 5-(p-propylsulfinyl)benzoyl-1,2-dihydro-3H-pyrrolo[1,2-a]pyrrole-1-carboxylate;

methyl 5-(o-isopropylsulfinyl)benzoyl-1,2-dihydro-3H-pyrrolo[1,2-a]pyrrole-1-carboxylate;

methyl 5-(m-isopropylsulfinyl)benzoyl-1,2-dihydro-3H-pyrrolo[1,2-a]pyrrole-1-carboxylate;

methyl 5-(p-butylsulfinyl)benzoyl-1,2-dihydro-3H-pyrrolo[1,2-a]pyrrole-1-carboxylate;

methyl 5-(o-isobutylsulfinyl)benzoyl-1,2-dihydro-3H-pyrrolo[1,2-a]pyrrole-1-carboxylate;

methyl 5-(m-isobutylsulfinyl)benzoyl-1,2-dihydro-3H-pyrrolo[1,2-a]pyrrole-1-carboxylate;

methyl 5-(p-isobutylsulfinyl)benzoyl-1,2-dihydro-3H-pyrrolo[1,2-a]pyrrole-1-carboxylate;

methyl 5-[m-(t-butylsulfinyl]benzoyl-1,2-dihydro-3H-pyrrolo[1,2-a]pyrrole-1-carboxylate; and methyl 5-[p-(t-butylsulfinyl)]benzoyl-1,2-dihydro-3H-pyrrolo[1,2-a]pyrrole-1-carboxylate.

C. In a similar fashion, by following the procedure of Part A of this example but substituting other alkyl carboxylates of Part C, Preparation 3 for methyl 5-(p-methylthio)benzoyl-1,2-dihydro-3H-pyrrolo[1,2-a]pyrrole-1-carboxylate, other compounds of this invention are prepared such as ethyl 5-(p-methylsulfinyl)benzoyl-1,2-dihydro-3H-pyrrolo[1,2-a]pyrrole-1-carboxylate;

propyl 5-(p-methylsulfinyl)benzoyl-1,2-dihydro-3H-pyrrolo[1,2-a]pyrrole-1-carboxylate;

isopropyl 5-(p-methylsulfinyl)benzoyl-1,2-dihydro-3H-pyrrolo[1,2-a]pyrrole-1-carboxylate;

butyl 5-(p-methylsulfinyl)benzoyl-1,2-dihydro-3H-pyrrolo[1,2-a]pyrrole-1-carboxylate;

isobutyl 5-(p-methylsulfinyl)benzoyl-1,2-dihydro-3H-pyrrolo[1,2-a]pyrrole-1-carboxylate;

t-butyl 5-(p-methylsulfinyl)benzoyl-1,2-dihydro-3H-pyrrolo[1,2-a]pyrrole-1-carboxylate; and the analogous lower alkyl esters of the compounds.

EXAMPLE 2

5-alkylsulfinylbenzoyl-1,2-dihydro-3H-pyrrolo[1,2-a]pyrrole-1-carboxylic acids

A. A mixture of methyl 5-(p-methylsulfinyl)-benzoyl-1,2-dihydro-3H-pyrrolo[1,2-a]pyrrole-1-carboxylate (6.9 mmol.), 13.8 mmol. (1.91 g) potassium carbonate, 40 ml of methanol and 10 ml of water is heated at reflux temperature in a nitrogen atmosphere for 15 minutes. After cooling to ambient temperature, the methanol is removed in vacuo and the residue is dissolved in 50 ml of water. This solution is washed with three 30 ml portions of ethyl acetate, acidified with 28 mmol. (3.55 g) oxalic acid, saturated with sodium chloride and extracted with ten 50 ml portions of ethyl acetate. The ethyl acetate extract is dried over sodium sulfate and the ethyl acetate removed by vacuum to give a crystalline product which is purified by crystallization from methanol to give 5-(p-methylsulfinyl)benzoyl-1,2-dihydro-3H-pyrrolo[1,2-a]pyrrole-1-carboxylic acid, m.p. 214°–215.5° C.

B. In a similar manner, by following the procedure of Part A. of this example but substituting other methyl 5-alkylsulfinylbenzoyl-1,2-dihydro-3H-pyrrolo[1,2-a]pyrrole-1-carboxylates as prepared according to Example 1, Part B for methyl 5-(p-methylsulfinyl)benzoyl-1,2-dihydro-3H-pyrrolo[1,2-a]pyrrole-1-carboxylate, other carboxylic acids of this invention are prepared such as 5-(o-methylsulfinyl)-benzoyl-1,2-dihydro-3H-pyrrolo[1,2-a]pyrrole-1-carboxylic acid;

5-(m-methylsulfinyl)benzoyl-1,2-dihydro-3H-pyrrolo[1,2-a]pyrrole-1-carboxylic acid;

5-(o-ethylsulfinyl)benzoyl-1,2-dihydro-3H-pyrrolo[1,2-a]pyrrole-1-carboxylic acid;

5-(m-ethylsulfinyl)benzoyl-1,2-dihydro-3H-pyrrolo[1,2-a]pyrrole-1-carboxylic acid;

5-(p-ethylsulfinyl)benzoyl-1,2-dihydro-3H-pyrrolo[1,2-a]pyrrole-1-carboxylic acid;

5-(p-propylsulfinyl)benzoyl-1,2-dihydro-3H-pyrrolo[1,2-a]pyrrole-1-carboxylic acid;

5-(o-isopropylsulfinyl)benzoyl-1,2-dihydro-3H-pyrrolo[1,2-a]pyrrole-1-carboxylic acid;

5-(m-isopropylsulfinyl)benzoyl-1,2-dihydro-3H-pyrrolo[1,2-a]pyrrole-1-carboxylic acid;

5-(p-butylsulfinyl)benzoyl-1,2-dihydro-3H-pyrrolo[1,2-a]pyrrole-1-carboxylic acid;

5-(o-isobutylsulfinyl)benzoyl-1,2-dihydro-3H-pyrrolo[1,2-a]pyrrole-1-carboxylic acid;

5-(m-isobutylsulfinyl)benzoyl-1,2-dihydro-3H-pyrrolo[1,2-a]pyrrole-1-carboxylic acid;

5-(p-isobutylsulfinyl)benzoyl-1,2-dihydro-3H-pyrrolo[1,2-a]pyrrole-1-carboxylic acid;

5-[m-(t-butylsulfinyl)]benzoyl-1,2-dihydro-3H-pyrrolo[1,2-a]pyrrole-1-carboxylic acid; and 5-[p-(t-butylsulfinyl)]benzoyl-1,2-dihydro-3H-pyrrolo[1,2-a]pyrrole-1-carboxylic acid.

EXAMPLE 3

5-alkylsulfonylbenzoyl-1,2-dihydro-3H-pyrrolo[1,2-a]pyrrole-1-carboxylates.

A. Three mmol. of m-chloroperbenzoic acid (0.518 g) are dissolved in 10 ml of chloroform and added, with stirring, to a solution of 1.51 mmol. methyl 5-(p-methylthio)benzoyl-1,2-dihydro-3H-pyrrolo[1,2-a]pyrrole-1-carboxylate (0.475 g) in 25 ml of chloroform while the solution is maintained at 0° C. After a half hour at 0° C., the reaction is washed successively with 20 ml of saturated sodium bicarbonate solution and twice with 15 ml portions of a saturated sodium chloride solution. The organic phase is dried over sodium sulfate and the solvent removed under reduced pressure. The residue is purified by thin layer chromatography on silca gel using hexane-ethyl acetate (35:65) as the developing solvent. Crystallization of the resulting product from a mixture of dichloromethane-ether gives 0.36 g of methyl 5-(p-methylsulfonyl)-benzoyl-1,2-dihydro-3H-pyrrolo[1,2-a]pyrrole-1-carboxylate, m.p. 130°–130.5° C.

B. In a similar manner, by following the procedure of Part A of this example but substituting other methyl 5-(p-alkylthio)benzoyl-1,2-dihydro-3H-pyrrolo[1,2-a]pyrrole-1-carboxylates for methyl 5-(p-methylthio)-benzoyl-1,2-dihydro-3H-pyrrolo[1,2-a]pyrrole-1-carboxylate, other compounds of the invention may be obtained such as methyl 5-(o-methylsulfonyl)benzoyl-1,2-dihydro-3H-pyrrolo[1,2-a]pyrrole-1-carboxylate;

methyl 5-(m-methylsulfonyl)benzoyl-1,2-dihydro-3H-pyrrolo[1,2-a]pyrrole-1-carboxylate;

methyl 5-(o-ethylsulfonyl)benzoyl-1,2-dihydro-3H-pyrrolo[1,2-a]pyrrole-1-carboxylate;

methyl 5-(m-ethylsulfonyl)benzoyl-1,2-dihydro-3H-pyrrolo[1,2-a]pyrrole-1-carboxylate;

methyl 5-(p-ethylsulfonyl)benzoyl-1,2-dihydro-3H-pyrrolo[1,2-a]pyrrole-1-carboxylate;

methyl 5-(p-propylsulfonyl)benzoyl-1,2-dihydro-3H-pyrrolo[1,2-a]pyrrole-1-carboxylate;

methyl 5-(o-isopropylsulfonyl)benzoyl-1,2-dihydro-3H-pyrrolo[1,2-a]pyrrole-1-carboxylate;

methyl 5-(m-isopropylsulfonyl)benzoyl-1,2-dihydro-3H-pyrrolo[1,2-a]pyrrole-1-carboxylate;

methyl 5-(p-butylsulfonyl)benzoyl-1,2-dihydro-3H-pyrrolo[1,2-a]pyrrole-1-carboxylate;

methyl 5-(o-isobutylsulfonyl)benzoyl-1,2-dihydro-3H-pyrrolo[1,2-a]pyrrole-1-carboxylate;

methyl 5-(m-isobutylsulfonyl)benzoyl-1,2-dihydro-3H-pyrrolo[1,2-a]pyrrole-1-carboxylate;

methyl 5-(p-isobutylsulfonyl)benzoyl-1,2-dihydro-3H-pyrrolo[1,2-a]pyrrole-1-carboxylate;

methyl 5-[m-(t-butylsulfonyl)]benzoyl-1,2-dihydro-3H-pyrrolo[1,2-a]pyrrole-1-carboxylate; and methyl 5-[p-(t-butylsulfonyl)]benzoyl-1,2-dihydro-3H-pyrrolo[1,2-a]pyrrole-1-carboxylate.

C. In a similar fashion, by following the procedure of Part A of this example but substituting other alkyl carboxylates of Part C, Preparation 3 for methyl 5-(p-methylthio)benzoyl-1,2-dihydro-3H-pyrrolo[1,2-a]pyrrole-1-carboxylate, other compounds of this invention are prepared such as ethyl 5-(p-methylsulfonyl)benzoyl-1,2-dihydro-3H-pyrrolo[1,2-a]pyrrole-1-carboxylate;

propyl 5-(p-methylsulfonyl)benzoyl-1,2-dihydro-3H-pyrrolo[1,2-a]pyrrole-1-carboxylate;

isopropyl 5-(p-methylsulfonyl)benzoyl-1,2-dihydro-3H-pyrrolo[1,2-a]pyrrole-1-carboxylate;

butyl 5-(p-methylsulfonyl)benzoyl-1,2-dihydro-3H-pyrrolo[1,2-a]pyrrole-1-carboxylate;

isobutyl 5-(p-methylsulfonyl)benzoyl-1,2-dihydro-3H-pyrrolo[1,2-a]pyrrole-1-carboxylate;

t-butyl 5-(p-methylsulfonyl)benzoyl-1,2-dihydro-3H-pyrrolo[1,2-a]pyrrole-1-carboxylate; and the analogous lower alkyl esters of the compounds.

EXAMPLE 4

5-alkylsulfonylbenzoyl-1,2-dihydro-3H-pyrrolo[1,2-a]pyrrole-1-carboxylic acids

A. A mixture of methyl 5-(p-methylsulfonyl)-benzoyl-1,2-dihydro-3H-pyrrolo[1,2-a]pyrrole-1-carboxylate (6.9 mmol.), 13.8 mmol. (1.91 g) potassium carbonate, 40 ml of methanol and 10 ml of water is heated at reflux temperature in a nitrogen atmosphere for 15 minutes. After cooling to ambient temperature, the methanol is removed in vacuo and the residue is dissolved in 50 ml of water. This solution is washed with three 30 ml portions of ethyl acetate, acidified with 28 mmol. (3.55 g) oxalic acid, saturated with sodium chloride and extracted with ten 50 ml portions of ethyl acetate. The ethyl acetate extract is dried over sodium sulfate and the ethyl acetate removed by vacuum to give a crystalline product which is purified by crystallization from methanol to give 5-(p-methylsulfonyl)benzoyl-1,2-dihydro-3H-pyrrolo[1,2-a]pyrrole-1-carboxylic acid, m.p. 214°–215.5° C.

B. In a similar manner, by following the procedure of Part A. of this example but substituting other methyl 5-(alkylsulfonyl)benzoyl-1,2-dihydro-3H-pyrrolo[1,2-a]pyrrole-1-carboxylates as prepared according to Example 3, Part B for methyl 5-(4-methylsulfonyl)benzoyl-1,2-dihydro-3H-pyrrolo[1,2-a]pyrrole-1-carboxylate, other carboxylic acids of this invention are prepared such as 5-(o-methylsulfonyl)benzoyl-1,2-dihydro-3H-pyrrolo[1,2-a]pyrrole-1-carboxylic acid;

5-(m-methylsulfonyl)benzoyl-1,2-dihydro-3H-pyrrolo[1,2-a]pyrrole-1-carboxylic acid;

5-(o-ethylsulfonyl)benzoyl-1,2-dihydro-3H-pyrrolo[1,2-a]pyrrole-1-carboxylic acid;

5-(m-ethylsulfonyl)benzoyl-1,2-dihydro-3H-pyrrolo[1,2-a]pyrrole-1-carboxylic acid;

5-(p-ethylsulfonyl)benzoyl-1,2-dihydro-3H-pyrrolo[1,2-a]pyrrole-1-carboxylic acid;

5-(p-propylsulfonyl)benzoyl-1,2-dihydro-3H-pyrrolo[1,2-a]pyrrole-1-carboxylic acid;

5-(o-isopropylsulfonyl)benzoyl-1,2-dihydro-3H-pyrrolo[1,2-a]pyrrole-1-carboxylic acid;

5-(m-isopropylsulfonyl)benzoyl-1,2-dihydro-3H-pyrrolo[1,2-a]pyrrole-1-carboxylic acid;

5-(p-butylsulfonyl)benzoyl-1,2-dihydro-3H-pyrrolo[1,2-a]pyrrole-1-carboxylic acid;

5-(o-isobutylsulfonyl)benzoyl-1,2-dihydro-3H-pyrrolo[1,2-a]pyrrole-1-carboxylic acid;

5-(m-isobutylsulfonyl)benzoyl-1,2-dihydro-3H-pyrrolo[1,2-a]pyrrole-1-carboxylic acid;

5-(p-isobutylsulfonyl)benzoyl-1,2-dihydro-3H-pyrrolo[1,2-a]pyrrole-1-carboxylic acid;

5-[m-(t-butylsulfonyl)]benzoyl-1,2-dihydro-3H-pyrrolo[1,2-a]pyrrole-1-carboxylic acid; and 5-[p-(t-butylsulfonyl)]benzoyl-1,2-dihydro-3H-pyrrolo[1,2-a]pyrrole-1-carboxylic acid.

EXAMPLE 5

1-cyano-5-alkylsulfonylbenzoyl-1,2-dihydro-3H-pyrrolo[1,2-a]pyrrole

A. A solution of 20 mmol. (3.73 g) of 4-methylthiobenzoylchloride and 10 mmol. (1.32 g) 1-cyano-1,2-dihydro-3H-pyrrolo[1,2-a]pyrrole (prepared as in Preparation 6) in 50 ml of dry toluene is heated at reflux temperature in a nitrogen atmosphere for 168 hours. The resulting solution is washed successively with one 100 ml portion of saturated sodium bicarbonate solution and two 50 ml portions of saturated sodium chloride solution then dried over sodium sulfate and evaporated in vacuo. The residue is chromatographed on 200 g of silica gel to give 0.72 g of a product which is eluted with hexane-ethyl acetate (1:1). Recrystallization from a mixture of methylene dichloride with ethyl ether gives 1-cyano-5-(p-methylthio)benzoyl-1,2-dihydro-3H-pyrrolo[1,2-a]pyrrole, m.p. 113°–113.5° C.

A solution of 20 ml of chloroform containing 4.1 mmol. (0.710 g) m-chloroperbenzoic acid is added slowly to a solution of 2.05 mmol. (0.580 g) of the methylthionitrile prepared as discussed immediately above in 25 ml of chloroform at 0° C. After 1 hour at 0° C., an additional 1 mmol. (0.172 g) of m-chloroperbenzoic acid is added and one-half hour thereafter the reaction mixture is poured into a 15 ml portion of saturated sodium bicarbonate solution. The organic phase is washed twice with 10 ml portions of a saturated sodium chloride solution, dried over sodium sulfate and the solvent removed under vacuum. The residue is crystallized from methylene dichloride-ethyl ether mixture to give 1-cyano-5-(p-methylsulfonyl)benzoyl-1,2-dihydro-3H-pyrrolo[1,2-a]pyrrole in a 94% yield (0.620 g), m.p. 183°–184° C. (with decomposition).

B. By following in principle the procedure of Part A but substituting other appropriate alkylthiobenzoyl chlorides for p-methylthiobenzoyl chloride, other 1-cyano-5-alkylthiobenzoyl-1,2-dihydro-3H-pyrrolo[1,2-a]pyrroles can be prepared such as 1-cyano-5-(m-methylsulfonyl)benzoyl-1,2-dihydro-3H-pyrrolo[1,2-a]pyrrole;

1-cyano-5-(o-methylsulfonyl)benzoyl-1,2-dihydro-3H-pyrrolo[1,2-a]pyrrole;

1-cyano-5-(p-ethylsulfonyl)benzoyl-1,2-dihydro-3H-pyrrolo[1,2-a]pyrrole;

1-cyano-5-(m-ethylsulfonyl)benzoyl-1,2-dihydro-3H-pyrrolo[1,2-a]pyrrole;

1-cyano-5-(o-ethylsulfonyl)benzoyl-1,2-dihydro-3H-pyrrolo[1,2-a]pyrrole;

1-cyano-5-(p-propylsulfonyl)benzoyl-1,2-dihydro-3H-pyrrolo[1,2-a]pyrrole;

1-cyano-5-(m-propylsulfonyl)benzoyl-1,2-dihydro-3H-pyrrolo[1,2-a]pyrrole;

1-cyano-5-(o-propylsulfonyl)benzoyl-1,2-dihydro-3H-pyrrolo[1,2-a]pyrrole;

1-cyano-5-(p-butylsulfonyl)benzoyl-1,2-dihydro-3H-pyrrolo[1,2-a]pyrrole;

1-cyano-5-(m-butylsulfonyl)benzoyl-1,2-dihydro-3H-pyrrolo[1,2-a]pyrrole;

1-cyano-5-(o-butylsulfonyl)-benzoyl-1,2-dihydro-3H-pyrrolo[1,2-a]pyrrole; and the like.

EXAMPLE 6

5-alkylsulfonylbenzoyl-1,2-dihydro-3H-pyrrolo[1,2-a]pyrrole-1-carboxylic acid

A. A solution of 1-cyano-5-(p-methylsulfonyl)-benzoyl-1,2-dihydro-3H-pyrrolo[1,2-a]pyrrole (0.62 g, 1.97 mmol.), 0.293 g potassium hydroxide, 50 ml ethanol and 5 ml water is heated at reflux temperature in a nitrogen atmosphere for 4 hours. At this time 586 mg more of potassium hydroxide are added and heating at reflux is continued for an additional 2 hours. The solution is cooled to ambient temperature, the ethanol is removed at reduced pressure and the residue is dissolved in 30 ml of water. The solution is washed three times with 30 ml portions of ethyl acetate, made acidic with hydrochloric acid and extracted ten times with 50 ml portions of ethyl acetate. The extract is dried over sodium sulfate and evaporated in vacuo to give a residue which then recrystallized from ethyl acetate-ether mixture gives 0.23 g (35% yield) of 5-(p-methylsulfonyl)benzoyl-1,2-dihydro-3H-pyrrolo[1,2-a]pyrrole-1-carboxylic acid, m.p. 211°–212° C.

B. In a similar manner by following the procedure of Part A of this example but substituting other appropriate 1-cyano-5-alkylsulfonylbenzoyl-1,2-dihydro-3H-pyrrolo[1,2-a]-pyrrole as prepared in Example 5 for 1-cyano-5-(p-methylsulfonyl)benzoyl-1,2-dihydro-3H-pyrrolo[1,2-a]pyrrole, other compounds of this invention are prepared such as 5-(m-methylsulfonyl)benzoyl-1,2-dihydro-3H-pyrrolo[1,2-a]pyrrole-1-carboxylic acid 5-(o-methylsulfonyl)-benzoyl-1,2-dihydro-3H-pyrrolo[1,2-a]pyrrole-1-carboxylic acid 5-(p-ethylsulfonyl)benzoyl-1,2-dihydro-3H-pyrrolo[1,2-a]pyrrole-1-carboxylic acid 5-(m-ethylsulfonyl)benzoyl-1,2-dihydro-3H-pyrrolo[1,2-a]pyrrole-1-carboxylic acid 5-(o-ethylsulfonyl)benzoyl-1,2-dihydro-3H-pyrrolo[1,2-a]pyrrole-1-carboxylic acid 5-(p-propylsulfonyl)benzoyl-1,2-dihydro-3H-pyrrolo[1,2-a]pyrrole-1-carboxylic acid 5-(m-propylsulfonyl)benzoyl-1,2-dihydro-3H-pyrrolo[1,2-a]pyrrole-1-carboxylic acid 5-(o-propylsulfonyl)benzoyl-1,2-dihydro-3H-pyrrolo[1,2-a]pyrrole-1-carboxylic acid 5-(p-butylsulfonyl)-benzoyl-1,2-dihydro-3H-pyrrolo[1,2-a]pyrrole-1-carboxylic acid 5-(m-butylsulfonyl)benzoyl-1,2-dihydro-3H-pyrrolo[1,2-a]pyrrole-1-carboxylic acid 5-(o-butylsulfonyl)benzoyl-1,2-dihydro-3H-pyrrolo[1,2-a]pyrrole-1-carboxylic acid and the like.

EXAMPLE 7

| Ingredients | Quantity per tablet, mg |
| --- | --- |
| 5-(p-methylsulfinyl)benzoyl-1,2-dihydro-3H-pyrrolo[1,2-a]pyrrole-1-carboxylic acid | 25 |
| cornstarch | 20 |
| lactose, spray-dried | 153 |
| magnesium stearate | 2 |

The above ingredients are thoroughly mixed and pressed into single scored tablets.

EXAMPLE 8

| Ingredients | Quantity per tablet, mg |
| --- | --- |
| 5-(p-methylsulfonyl)benzoyl-1,2-dihydro-3H-pyrrolo[1,2-a]pyrrole-1-carboxylic acid | 108 |
| lactose | 15 |
| cornstarch | 25 |
| magnesium stearate | 2 |

The above ingredients are mixed and introduced into a hard-shell gelatin capsule.

EXAMPLE 9

| Ingredients | Quantity per tablet, mg |
| --- | --- |
| 5-(p-methylsulfinyl)benzoyl-1,2-dihydro-3H-pyrrolo[1,2-a]pyrrole-1-carboxylic acid | 115 |
| lactose | 93 |
| cornstarch | 40 |
| magnesium stearate | 2 |

The above ingredients are mixed and introduced into a hard-shell gelatin capsule.

EXAMPLE 10

| Ingredients | Quantity |
| --- | --- |
| 5-(p-methylsulfonyl)benzoyl-1,2-dihydro-3H-pyrrolo[1,2-a]pyrrole-1-carboxylic acid | 0.2 g |
| $K_2HPO_4$ buffer (0.4 M solution) | 2 ml |
| KOH (1N) | qs. to pH7 |
| water (distilled sterile) | qs. to 20 ml |

0.1 G. of 5-(p-methylsulfonyl)benzoyl-1,2-dihydro-3H-pyrrolo[1,2-a]pyrrole-1-carboxylic acid is substituted for the 0.2 g of the compound of the above composition.

EXAMPLE 11

A suppository totaling 2.8 grams is prepared having the following composition:

| | |
| --- | --- |
| 5-(p-methylsulfinyl)benzoyl-1,2-dihydro-3H-pyrrolo[1,2-a]pyrrole-1-carboxylic acid | 25 mg |

-continued

| | |
|---|---|
| Witepsol H-15 (triglycerides of saturated vegetable fatty acids; a product of Riches-Nelson, Inc., New York, N.Y. | balance |

12.5 Mg of 5-(p-methylsulfonyl)benzoyl-1,2-dihydro-3H-pyrrolo[1,2-a]pyrrole-1-carboxylic acid is substituted for the 25 mg of the compound of the above composition.

EXAMPLE 12

An oral suspension for pediatric use is prepared having the following composition:

| | |
|---|---|
| 5-(p-methylsulfinyl)benzoyl-1,2-dihydro-3H-pyrrolo[1,2-a]pyrrole-1-carboxylic acid | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavorings | 0.035 ml |
| colorings | 0.5 mg |
| distilled water | qs. to 100 ml |

0.05 G. of 5-(p-methylsulfonyl)benzoyl-1,2-dihydro-3H-pyrrolo[1,2-a]pyrrole-1-carboxylic acid is substituted for the 0.1 g of the compound of the above composition.

EXAMPLE 13–14

Powdered top dressings for veterinary use are prepared having the following compositions:

| | Ex. 13 | Ex. 14 |
|---|---|---|
| 5-(p-methylsulfinyl)benzoyl-1,2-dihydro-3H-pyrrolo-[1,2-a]pyrrole-1-carboxylic acid | 0.1 g | 1.2 g |
| sucrose | 5.7 g | 3.7 g |
| polyvinyl pyrrolidone | 0.3 g | 0.3 g |

0.05 G. of 5-(p-methylsulfonyl)benzoyl-1,2-dihydro-3H-pyrrolo[1,2-a]pyrrole-1-carboxylic acid is substituted for the 0.1 g of the compound of the composition of Example 13.

0.6 G. of 5-(p-methylsulfonyl)benzoyl-1,2-dihydro-3H-pyrrolo[1,2-a]pyrrole-1-carboxylic acid is substituted for the 1.2 g of the compound of the composition of Example 14.

The subject matter claimed is:

1. A compound selected from the group of those represented by the formula:

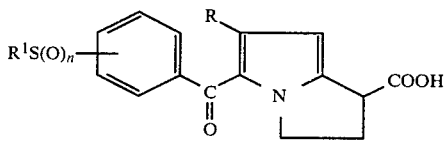

and the pharmaceutically acceptable, non-toxic alkyl esters having from one to 12 carbon atoms and salts thereof, wherein n is 1 or 2, R represents hydrogen or a lower alkyl group having from 1 to 4 carbon atoms and $R^1$ represents lower alkyl group having from 1 to 4 carbon atoms at the ortho, meta or para positions of the aroyl group.

2. A compound of claim 1 wherein R is hydrogen.

3. A compound of claim 2 wherein $R^1$ is methyl.

4. A compound of claim 3 wherein $R^1$ is methyl, n is 1 and the $R^1S(O)$ substituent is at the p-position.

5. A carboxylic acid compound of claim 4, namely 5-(p-methylsulfinyl)benzoyl-1,2-dihydro-3H-pyrrolo[1,2-a]pyrrole-1-carboxylic acid.

6. A methyl ester of the compound of claim 4, namely methyl 5-(p-methylsulfinyl)benzoyl-1,2-dihydro-3H-pyrrolo[1,2-a]pyrrole-1-carboxylate.

7. A carboxylic acid of the compound of claim 3 wherein n is 2, namely isopropyl 5-(p-methylsulfonyl)-benzoyl-1,2-dihydro-3H-pyrrolo[1,2-a]pyrrole-1-carboxylate.

8. A compound of claim 1 wherein the $R^1S(O)_n$ substituent is at the para-position of the phenyl ring.

9. A compound of claim 8 wherein $R^1$ is methyl.

10. The compound of claim 9 wherein R is methyl.

11. A carboxylic acid of claim 10 wherein n is 1, namely 5-(p-methylsulfinyl)benzoyl-6-methyl-1,2-dihydro-3H-pyrrolo[1,2-a]pyrrole-1-carboxylic acid.

12. A carboxylic acid of the compound of claim 10 wherein n is 2, namely methyl-5-(p-methylsulfonyl)-benzoyl-6-methyl-1,2-dihydro-3H-pyrrolo[1,2-a]pyrrole-1-carboxylate.

13. A composition for treating inflammation, pain or pyrexia in mammals consisting essentially of a pharmaceutically acceptable non-toxic excipient and a therapeutically effective amount of a compound of claim 1.

14. A method of treating inflammation, pain or pyrexia in mammals which comprises administering to a mammal suffering therefrom a therapeutically effective amount of a compound of claim 1.

15. A composition for administration to a pregnant mammal to delay onset of parturition consisting essentially of a pharmaceutically acceptable non-toxic excipient and a therapeutically effective amount of a compound of claim 1.

16. A method comprising administering to a pregnant mammal to delay the onset of parturition a therapeutically effective amount of a compound of claim 1.

17. The method of claim 16 wherein said pregnant mammal is a woman who is not suffering from inflammation, pyrexia, or pain.

18. The method of claim 17 wherein said pregnant woman has had a previous spontaneous abortion, miscarriage or premature delivery, which occurred prior to the time for normal parturition at or about full term.

19. The method of claim 16 wherein said pregnant mammal is a woman who is not suffering from inflammation, pyrexia or nonparturition-causing pain but who is experiencing uterine muscle contractions, said compound being administered in a therapeutically effective amount adapted to reduce the intensity or duration of the uterine muscle contractions or stop the uterine muscle contractions altogether, whereby termination of the pregnancy is postponed from the time it otherwise would have happened.

* * * * *